United States Patent
Narkhede

(10) Patent No.: US 11,369,430 B2
(45) Date of Patent: Jun. 28, 2022

(54) VESSEL SEALER HAVING UNIFORM PRESSURE MECHANISM, DETACHABLE BLADE/CUTTER AND DETACHABLE JAW ASSEMBLY

(71) Applicant: XCELLANCE MEDICAL TECHNOLOGIES PVT LTD, Navi Mumbai (IN)

(72) Inventor: Pradip Barsu Narkhede, Navi Mumbai (IN)

(73) Assignee: XCELLANCE MEDICAL TECHNOLOGIES PVT LTD, Navi Mumbai (IN)

( * ) Notice: Subject to any disclaimer, the term of this patent is extended or adjusted under 35 U.S.C. 154(b) by 632 days.

(21) Appl. No.: 16/323,690

(22) PCT Filed: Oct. 15, 2017

(86) PCT No.: PCT/IN2017/050474
§ 371 (c)(1),
(2) Date: Feb. 6, 2019

(87) PCT Pub. No.: WO2018/078646
PCT Pub. Date: May 3, 2018

(65) Prior Publication Data
US 2019/0175259 A1 Jun. 13, 2019

(30) Foreign Application Priority Data
Oct. 24, 2016 (IN) .............................. 201621036349

(51) Int. Cl.
*A61B 18/14* (2006.01)
*A61B 17/00* (2006.01)
(Continued)

(52) U.S. Cl.
CPC .......... *A61B 18/1445* (2013.01); *A61B 17/29* (2013.01); *A61B 17/295* (2013.01);
(Continued)

(58) Field of Classification Search
CPC .. A61B 2017/0046; A61B 2017/00464; A61B 2017/00473; A61B 2017/2845;
(Continued)

(56) References Cited

U.S. PATENT DOCUMENTS 5,507,297 A * 4/1996 Slater ..................... A61B 17/29
600/564
2011/0077649 A1 * 3/2011 Kingsley ............ A61B 18/1445
606/52

(Continued)

*Primary Examiner* — Daniel W Fowler
*Assistant Examiner* — Bradford C. Blaise
(74) *Attorney, Agent, or Firm* — Taft Stettinius & Hollister LLP; Derek B. Lavender; Roshan P. Shrestha

(57) ABSTRACT

A vessel sealer having a uniform pressure mechanism, detachable blade/cutter and detachable jaw assembly is disclosed. A bipolar surgical instrument, includes a jaw assembly having jaws connected to an outer tube, wherein the blade is connected to the blade pushing tube through a blade connector; a spring cap operatively engages said blade tube assembly wherein on disengagement of the said jaw assembly from an outer tube and said spring cap from said blade pushing tube are adapted to be detached from each other; a handle assembly, operatively coupled to said jaw assembly comprising a uniform pressure mechanism which contains primary spring, a secondary spring, wherein said uniform pressure mechanism enables closure of the jaws to ensure and exert a uniform pressure on the tissue and/or vessel.

9 Claims, 9 Drawing Sheets

(51) Int. Cl.
*A61B 18/00* (2006.01)
*A61B 90/00* (2016.01)
*A61B 17/29* (2006.01)
*A61B 17/295* (2006.01)

(52) U.S. Cl.
CPC ............... *A61B 2017/0046* (2013.01); *A61B 2017/2901* (2013.01); *A61B 2017/294* (2013.01); *A61B 2017/2919* (2013.01); *A61B 2017/2939* (2013.01); *A61B 2018/00589* (2013.01); *A61B 2018/00607* (2013.01); *A61B 2018/1452* (2013.01); *A61B 2018/1455* (2013.01); *A61B 2090/0813* (2016.02)

(58) Field of Classification Search
CPC .... A61B 2017/2901; A61B 2017/2908; A61B 2017/2913; A61B 2017/2919; A61B 2017/292; A61B 2017/2926; A61B 2017/2931; A61B 2017/2932; A61B 2017/2933; A61B 2017/2939; A61B 2017/294; A61B 17/28; A61B 17/285; A61B 17/29; A61B 17/2909; A61B 17/295; A61B 2018/00053; A61B 2018/00196; A61B 2018/00589; A61B 2018/00601; A61B 2018/00607; A61B 2018/0063; A61B 2018/0091; A61B 2018/0231; A61B 2018/1452; A61B 2018/1455; A61B 18/1442; A61B 18/1445; A61B 18/1447; A61B 90/08; A61B 2090/0813
See application file for complete search history.

(56) References Cited

U.S. PATENT DOCUMENTS

| | | | | |
|---|---|---|---|---|
| 2012/0078289 | A1* | 3/2012 | Livneh | A61B 17/29 606/205 |
| 2012/0232338 | A1* | 9/2012 | Livneh | A61B 18/1445 600/104 |
| 2013/0253480 | A1* | 9/2013 | Kimball | A61B 17/320092 606/1 |
| 2016/0089175 | A1* | 3/2016 | Hibner | A61B 17/285 606/206 |
| 2016/0100882 | A1* | 4/2016 | Boudreaux | A61B 18/1445 606/52 |
| 2017/0273735 | A1* | 9/2017 | Ding | A61B 18/1445 |

* cited by examiner

SECTION A-A

VESSEL SEALER HAVING UNIFORM PRESSURE MECHANISM, DETACHABLE BLADE/CUTTER AND DETACHABLE JAW ASSEMBLY

FIELD OF THE INVENTION

The present invention relates, in general to a surgical instrument and more particularly, to a surgical instrument having a jaw assembly that can be detached from an outer tube and a blade pushing tube by using a simple spring cap mechanism. The surgical instrument also include a blade/cutter that can be detached from a blade/cutter connector and further detached from the jaw assembly for the purpose of disposing it or reusing it after cleaning, while the handle assembly can be reused. Further, the present invention also relates to a uniform pressure mechanism which exerts uniform pressure on tissue/vessel irrespective of variation in pressure exerted by surgeon.

BACKGROUND

In monopolar devices, RF energy passes from a surgical area and a surgical instrument (monopolar device) through the patient's body to separate electrodes attached to a large surface area. In monopolar electrosurgery, there is a greater potential of injury to body tissues as the electrical current passes through them to the surface or return electrode. Skin burns can also occur at the site of the return electrode.

Bipolar electrosurgical products provide an improved margin of patient safety in certain minimally invasive surgical and interventional procedures. In bipolar devices, the RF energy is contained at the surgical site because both the active and return electrodes are located on the surgical instrument itself.

Various instruments have been used in various surgical procedures to seal with high frequency bipolar electric current and cut the tissue with a mechanical blade. Cutting with the mechanical blade does not require any electrical energy, whereby it can be cut with a single stroke of cutter blade movement. However, such blade upon multiple uses becomes distorted or unclean due to blood and tissue exposure, and thereby requires the removal for either disposing purpose or cleaning purpose.

Many of such blades are available in the prior-art; however they are mainly for one time use because they cannot be cleaned and autoclaved as a whole or in parts. Because the parts cannot be separated and the instrument has to be completely disposed, it increases the overall cost to buy a new instrument all together. Further, sometimes the blade gets blunt by cutting the tissue and becomes ineffective and hence no reuse is possible because blade is fixed with a jaw assembly. The other instruments where the blade can be separated from the instrument display a tougher mechanism of separating it.

This invention discloses an instrument that allows an easy mechanism for removal of the jaw assembly and detaching it from the outer tube and blade pushing tube for the purpose of disposing it or reusing it after cleaning it or autoclaving it.

The handle assembly of the instrument is reusable making it cost effective for the user. The blade/cutter can be disposed or sterilized and reused.

There are springs that allows for a full and perfect closure of the jaws to ensure and exert a uniform pressure on the tissue and/or vessel beyond which pressure the jaws cannot close thereby preventing injury to the tissue.

SUMMARY OF THE INVENTION

Vessel sealer having a uniform pressure mechanism, detachable blade/cutter and detachable jaw assembly is disclosed. A bipolar surgical instrument, includes a jaw assembly having jaws connected to an outer tube, wherein the blade is connected to the blade pushing tube through a blade connector; a spring cap operatively engages said blade tube assembly, wherein on disengagement of the jaw assembly from an outer tube and said spring cap from said blade pushing tube are adapted to be detached from each other; a handle assembly, operatively coupled to said jaw assembly comprising a uniform pressure mechanism which contains primary spring, a secondary spring, wherein said uniform pressure mechanism enables closure of the jaws to ensure and exert a uniform pressure on the tissue and/or vessel.

This invention relates to an easy mechanism which enables detachment of the jaw assembly from an outer tube and a blade pushing tube. The jaw assembly can then be cleaned or autoclaved and reused or the jaw assembly is disposed and replaced with another jaw assembly.

This invention further allows for an easy mechanism for the separation of the parts of the instrument. When the spring cap is removed, the whole jaw assembly can be detached.

When the spring cap is removed, the outer tube can be detached from the threaded joint of the sealing jaws. The blade is then detached from the blade connector and unlocked from the groove.

The blade pushing tube is then detached from the threaded joint of the blade connector separating it from the jaw assembly and eventually separating all the parts of the assembly.

The primary and secondary spring allows full and perfect closure of the jaws to ensure and exert a uniform pressure on the tissue and/or vessel beyond which pressure, the jaws cannot close thereby preventing injury to the tissue and allowing only a certain uniform maximum pressure on the tissue and/or vessel to seal it without damaging the other tissue and/or vessel.

DESCRIPTION

This particular invention discloses a bipolar surgical instrument having an easy and convenient mechanism that allows for removal of the cutter/blade and detach it from the jaw assembly for the purpose of disposing only the cutter or blade if it gets distorted or if it becomes blunt and replacing it with another cutter or blade since using the cutter/blade repetitively causes the sharpness to become less. The cutter/blade can be sterilized and reused.

The inner parts of the instrument require cleaning to make it sterile for another use. The cutter or blade can be reused after cleaning it or after autoclaving it.

This invention further discloses an instrument that allows removal of the jaw assembly and detaching it from the outer tube and blade pushing tube for the purpose of disposing it or reusing it after cleaning it or autoclaving it.

The handle assembly of the instrument is reusable making it cost effective for the user.

This invention further discloses an easy mechanism for completely detaching the jaw assembly that can be autoclaved and sterilized and can be attached easily for reuse with the same parts used previously or attached with other new parts.

Figure 1:
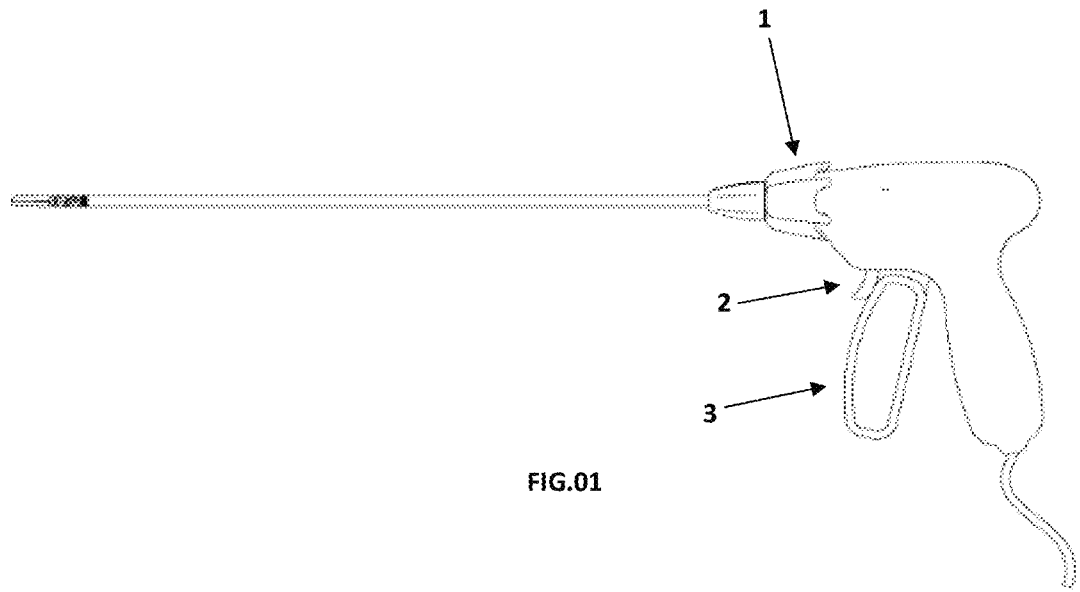
FIG. 1 illustrates the front view of the surgical instrument.

FIG. 1 illustrates the front view of the surgical instrument displaying the rotary knob 1, blade trigger 2 and jaw trigger 3.

Figure 2:
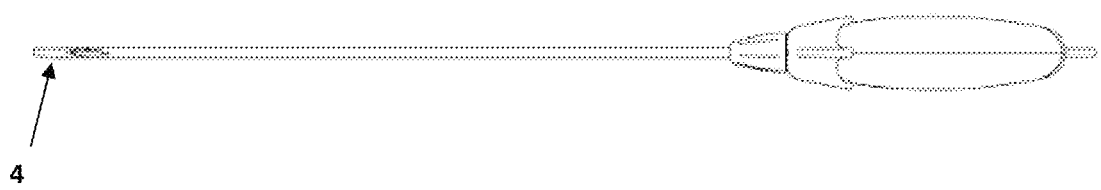
FIG. 2 illustrates the top view of the surgical instrument.

FIG. 2 illustrates the top view of the surgical instrument displaying the sealing jaws 4 of the jaw assembly.

Figure 3:
FIG. 3 illustrates the side view of the surgical instrument.

FIG. 3 illustrates the side view of the surgical instrument.

Figure 4:
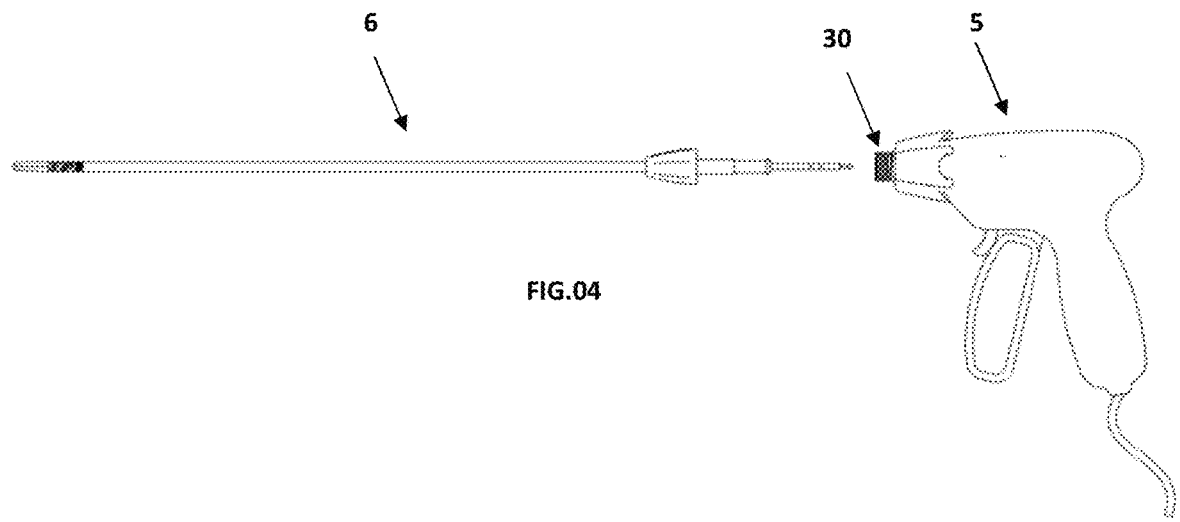
FIG. 4 illustrates the detachment of the front assembly with the handle assembly.

FIG. 4 illustrates the front view showing handle assembly 5 and the front working assembly 6 of the surgical instrument.

The front working assembly 6 can be detached from threaded joint 30 and removed from the handle assembly 5.

Figure 5:
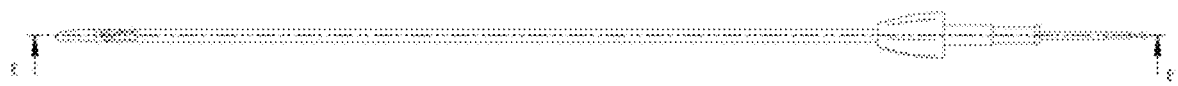
FIG. 5 illustrates the front working assembly showing the sectional view E in FIG. 6.
Figure 6:
FIG. 6 illustrates the detailed view F of the front region of the front working assembly in FIG. 7 and also illustrates the detailed view G of the back region the front working assembly in FIG. 8 showing the rotary knob and the parts within and behind the rotary knob.

FIG. 5 illustrates the front working assembly 6 showing the sectional view E in FIG. 6.

Figure 7:
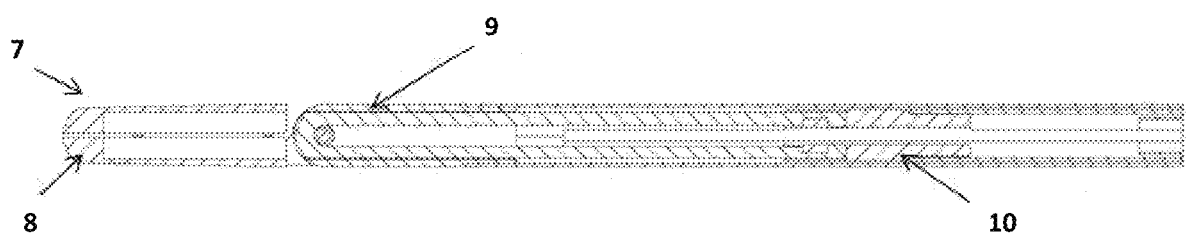
FIG. 7 illustrates the upper jaw and the lower jaw with the blade/cutter joined to the blade connector.
Figure 8:
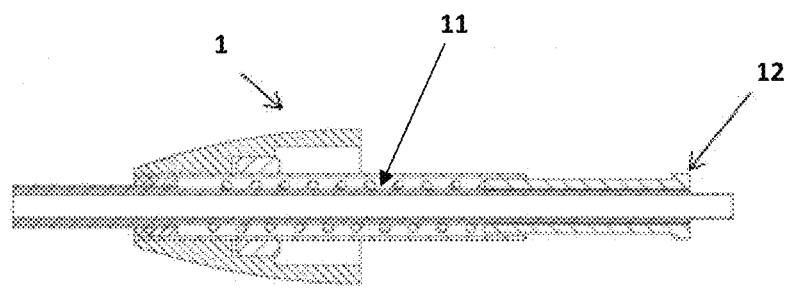
FIG. 8 illustrates the detailed view of rotary knob along with a blade spring and spring cap.

FIG. 6 illustrates the detailed view F of the front region of the front working assembly 6 in FIG. 7 and also illustrates the detailed view G of the back region the front working assembly 6 in FIG. 8 showing the rotary knob and the parts within and behind the rotary knob.

FIG. 7 illustrates the upper jaw 7 and the lower jaw 8 with the blade/cutter 9 joined to the blade connector 10.

The blade/cutter 9 can be detached from the blade/cutter connector 10. This ensures that the blade/cutter 9 is removed through the jaw assembly 19 (shown in FIG. 9) and separated from it for cleaning purpose so that the surgeon is able to reuse it or he can dispose it. The handle assembly 5 is reusable.

FIG. 8 illustrates the rotary knob 1 along with a blade spring 11 and spring cap 12. The blade spring 11 and spring cap 12 are connected to each other co-axially. Blade spring is placed within the rotary knob. The blade spring 11 and the spring cap 12 allow the blade to move to and fro on applying the blade trigger 2.

Figure 9:
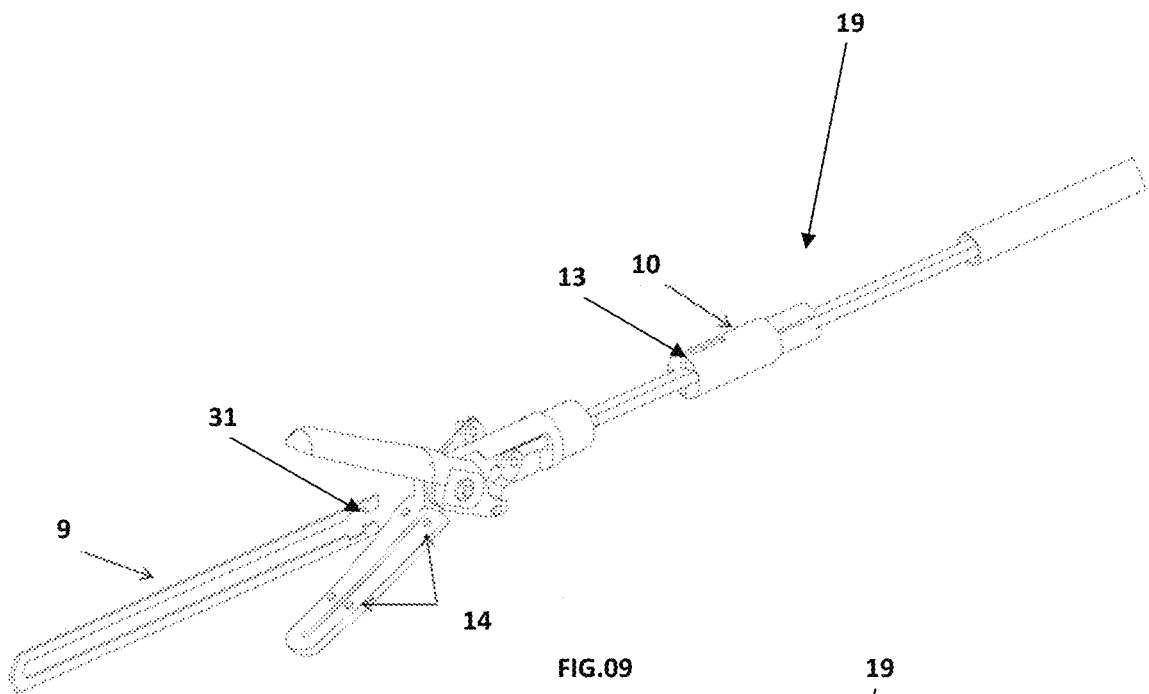
FIG. 9 illustrates the blade/cutter that can be detached from the blade/cutter connector.

FIG. 9 illustrates the blade/cutter 9 that can be detached from the blade/cutter connector 10 by pulling it out from the groove 13 and separated from the jaw assembly 19. The dents 31 on the blade on attachment mode locks in the groove 13 on the blade connector 10 which ensures tight locking that does not allow it to come out during the procedure. The jaws contain ceramic spacers 14.

Figure 10:
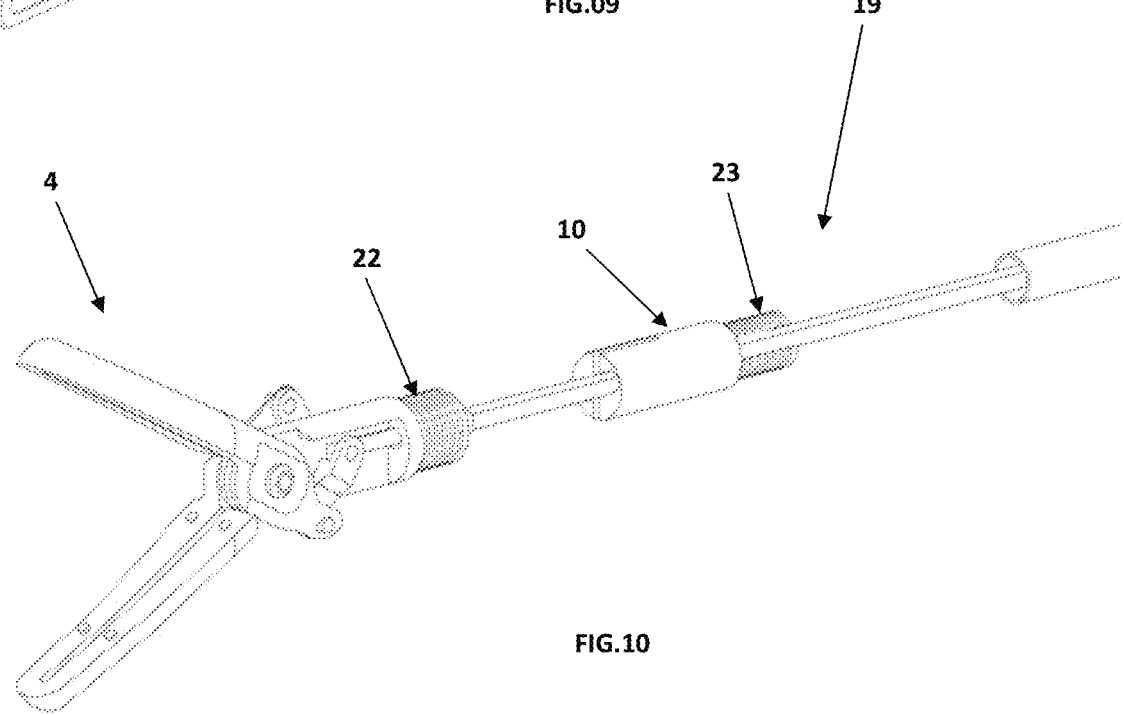
FIG. 10 illustrates the two threaded joints on the jaw assembly.

FIG. 10 illustrates the two threaded joints 22, 23 on the jaw assembly 19. The threaded joint 23 is attached to the blade connector 10. The threaded joint 22 is attached to the sealing jaws 4.

Figure 11:
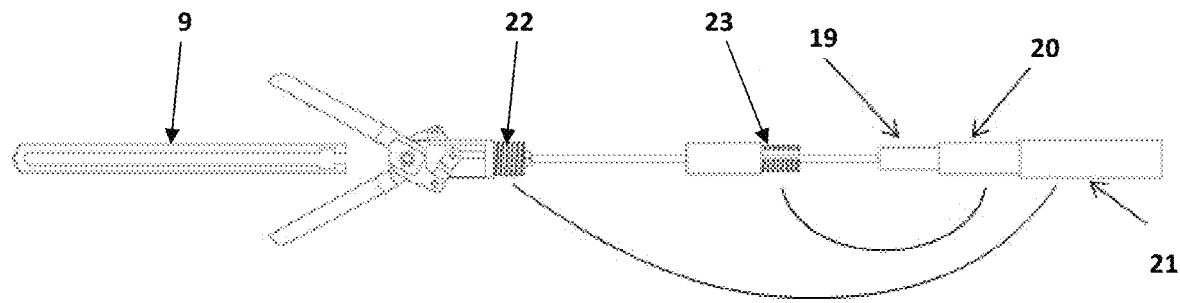
FIG. 11 illustrates the three alignments, the outer tube, the jaw assembly, the blade pushing tube.

FIG. 11 illustrates the three alignments, the outer tube 21, the jaw assembly 19, the blade pushing tube 20. The outer tube 21 is detachably fixed to the threaded joint 22; blade pushing tube 20 is detachably fixed to threaded joint 23.

Figure 12:
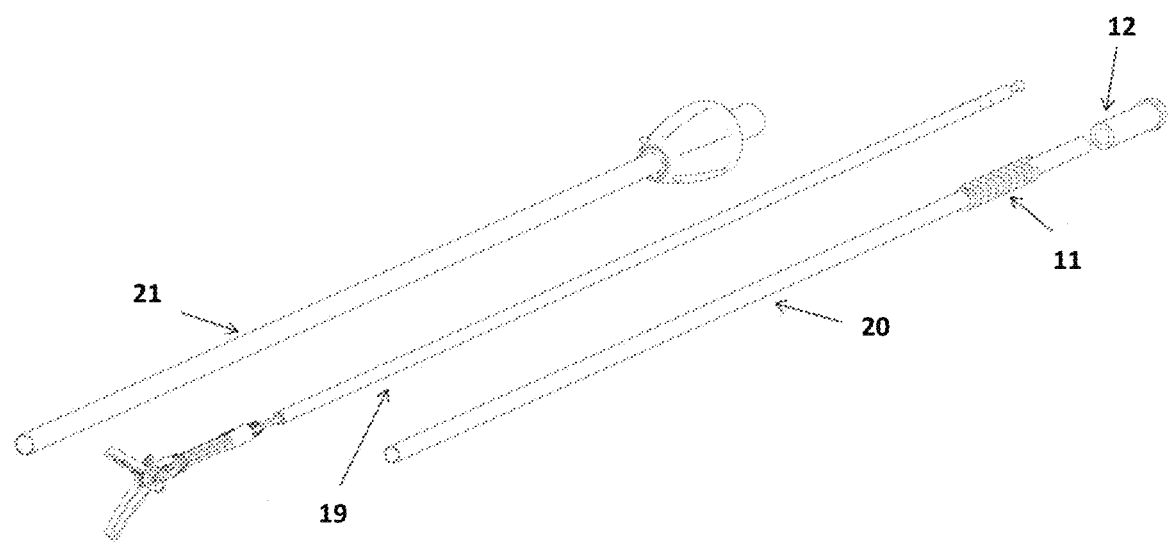
FIG. 12 illustrates an exploded view, showing the spring cap and an easy mechanism of separating all the parts.

FIG. 12 illustrates an exploded view, showing the spring cap 12 and an easy mechanism of separating all the parts of the jaw assembly by just removing the spring cap initially. When the spring cap 12 is removed, the whole jaw assembly can be detached.

When the spring cap is removed, the outer tube 21 can be detached from the threaded joint 22 of the sealing jaws. The blade is then detached from the blade connector 10 and unlocked from the groove 13 (shown in FIG. 9).

The blade pushing tube 20 is then detached from the threaded joint 23 of the blade connector 10 separating it from the jaw assembly 19 and eventually separating all the parts of the assembly.

The outer tube 21 is assembled on top of the blade/cutter 9 (shown in FIG. 11) the outer tube 21 restricts the detachment of the blade/cutter 9 due to the exact circumference thickness of the outer tube assembled exactly on top of the blade/cutter. Only when the outer tube 21 is removed, the blade can be detached from the blade connector 10. The blade/cutter 9 is then removed through the jaw assembly 19.

The blade pushing tube 20 consists of blade spring 11 and spring cap 12 that guides the blade movement when the blade trigger 2 is pressed.

The jaw assembly 19 can be reusable after cleaning it or it can be disposed after using it or the blade/cutter 9 can be disposed if distorted or reused after cleaning it. The handle assembly 5 is reusable. The reusable handle assembly makes the product cost effective.

Figure 13:
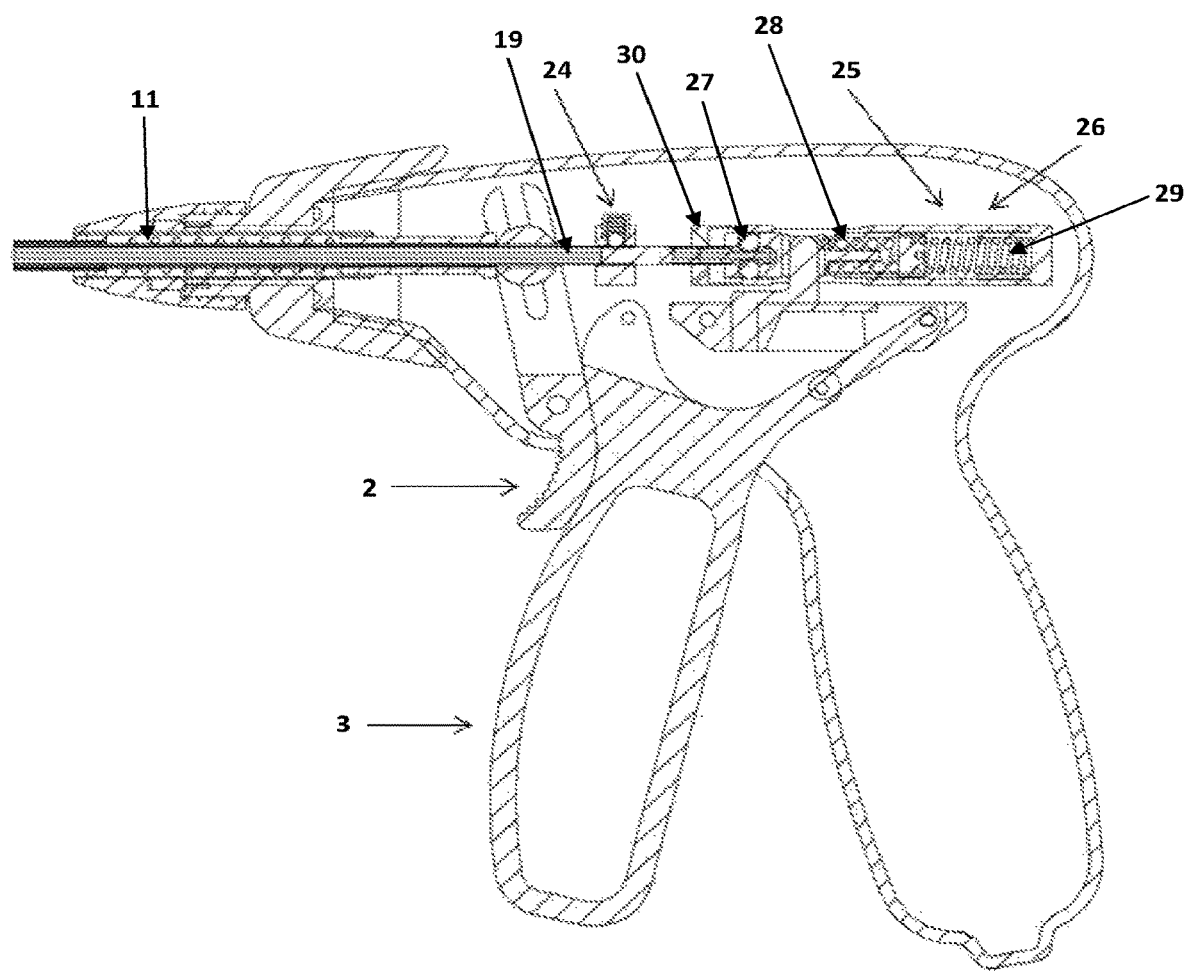
FIG. 13 illustrates the handle assembly, with the first contact and the second contact and the uniform pressure mechanism.

FIG. 13 illustrates the handle assembly, with the first contact 24 and the second contact 25. There can be numerous such insert contacts which can allow numerous applications. The portion 26 allows for uniform pressure to be applied between the jaws when the jaw trigger 3 is pressed. The jaw trigger 3 causes movements of the jaw insert tube when the trigger is pressed. The blade spring 11 allows the blade to move to and fro on applying the blade trigger 2 to cut the tissue and/or vessel.

The spring allows full and perfect closure of the jaws to ensure and exert a uniform pressure on the tissue and/or vessel beyond which pressure the jaws cannot close thereby preventing injury to the tissue and allowing only a certain uniform maximum pressure on the tissue and/or vessel to seal it without damaging the other tissue and/or vessel.

Figure 14:
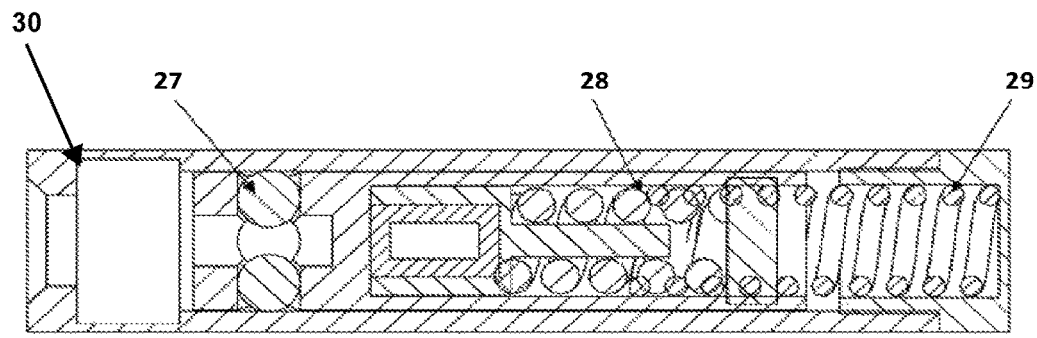
FIG. 14 illustrates a sectional view A-A of portion 26 displayed in FIG. 13.

FIG. 14 (Sectional view A-A of portion 26 displayed in FIG. 13) illustrates one primary spring 29, one secondary spring 28, and jaw lock balls 27 that are inside the portion 26 which causes the application of uniform pressure when the jaws are closed thereby preventing extra pressure or over pressure on the tissue and/or vessel.

When both the jaws are closed, they exert a pressure on the primary spring 29. On further closure of the jaws the extra pressure on jaws is absorbed by the secondary spring 28 by which both the springs compress when the trigger 1 is pressed. The secondary spring being hard absorbs the extra pressure induced by the primary spring, thereby creating a uniform pressure on both the jaws.

The jaw lock balls 27 pushed by the jaw assembly 19 and expands outwardly to the front region of the cam 30. When the jaw assembly 19 moves inwards it pushes the jaw lock balls 27 in and slide the balls in a non-expanded state inwardly to the back of the cam 30 such that the jaw assembly 19 is locked in between the balls. The cam 30 acts as an enclosure to move the balls to and fro.

Figure 15:
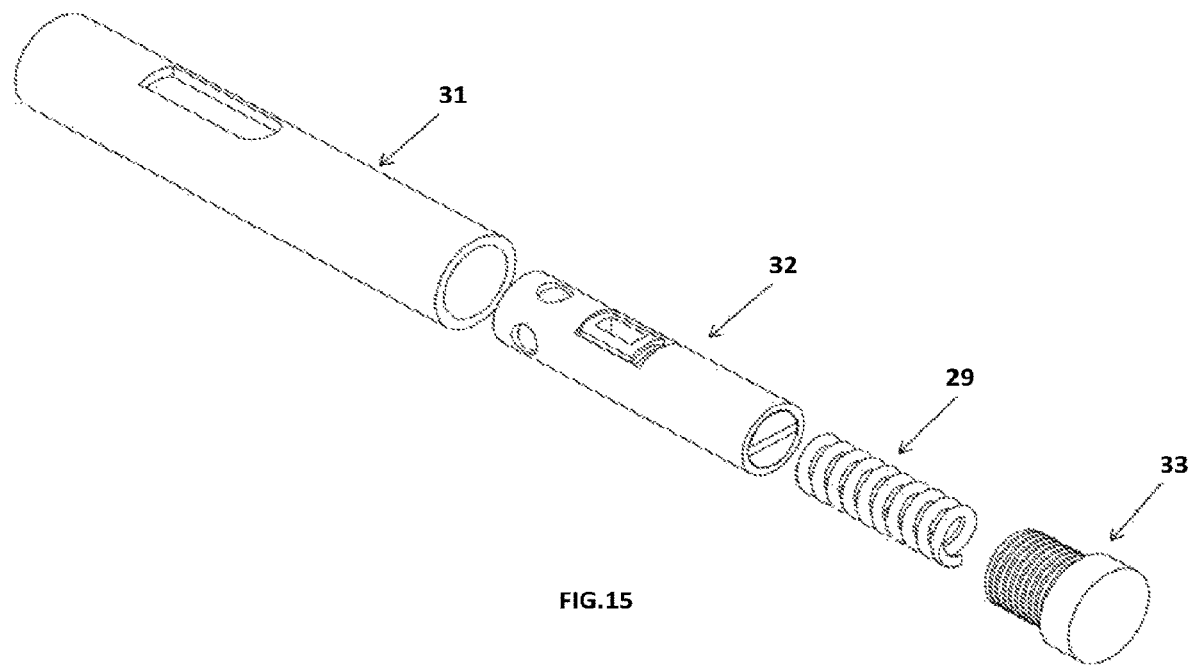
FIG. 15 illustrates an exploded view of the various parts displaying the outer casing, the inner casing assembly, the primary spring and the cap.

FIG. 15 illustrates an exploded view of the various parts displaying the outer casing 31, the inner casing assembly 32, the primary spring 29 and the cap 33.

Figure 16:
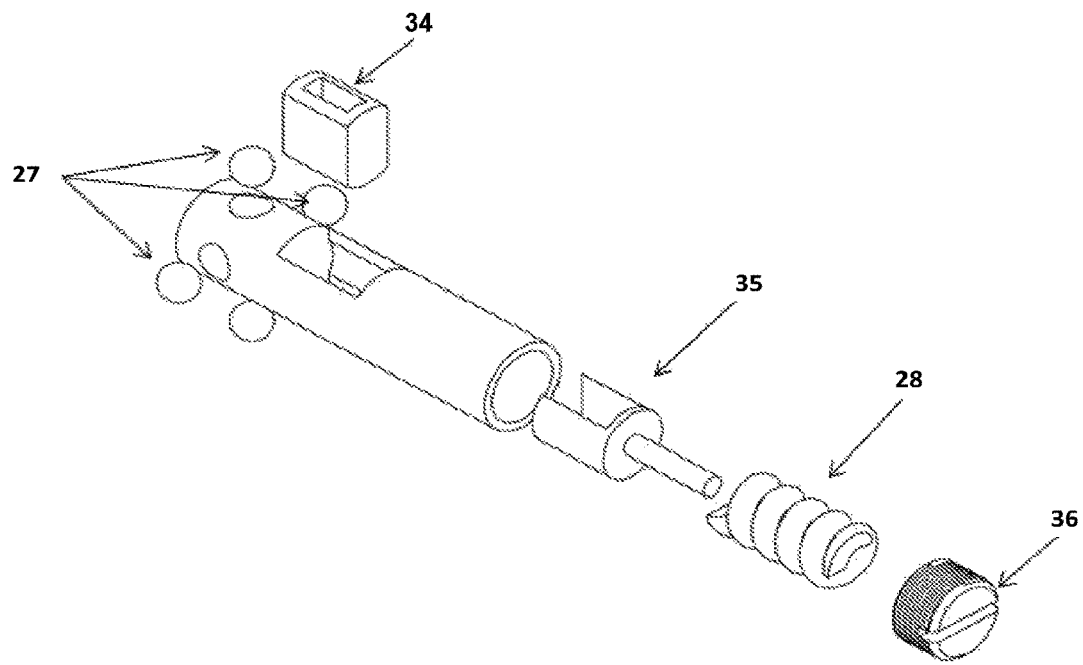
FIG. 16 illustrates an exploded view of the various parts displaying the inner casing that has the jaw locking balls and bush in it followed by the connector, the secondary spring and cap.

FIG. 16 illustrates an exploded view of the various parts displaying the inner casing 32 that has the jaw locking balls 27 and bush 34 in it followed by the connector 35, the secondary spring 28 and cap 36.

Minimum two contact poles are needed to deliver bipolar energy delivery path. Various effects can be created by multiple poles or multiple poles can change the effect of the instrument.

Figure 17:
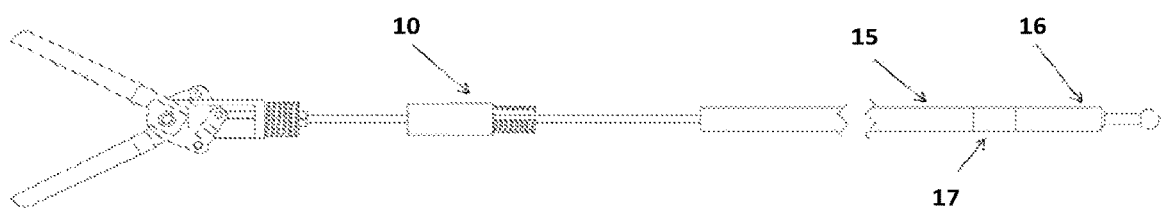
FIG. 17 illustrates the tube where the first contact pole in the handle causes electrical conduction on the first insert contact 15; second contact pole on the handle causes electrical conduction on second insert contact.

FIG. 17 illustrates the tube where the first contact pole 24 in the handle causes electrical conduction on the first insert contact 15; second contact pole 25 on the handle causes electrical conduction on second insert contact 16. Insulation 17 is provided in between both the contacts. The contacts cause electrical conduction on the jaws to seal the tissue and/or vessel.

Insulation can be more than one to prevent conduction of current on the surface of insert tube and outer tube.

Figure 18:
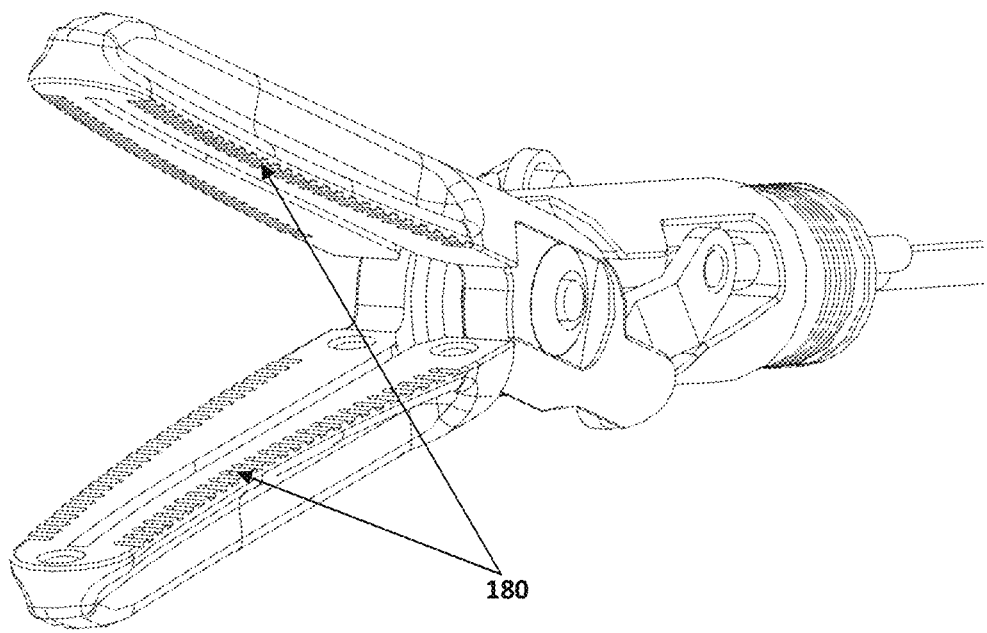
FIG. 18 illustrates exemplary jaws having serrations to have a better grip on a tissue.

FIG. 18 illustrates exemplary jaws having serrations to have a better grip on a tissue.

Figure 19A:
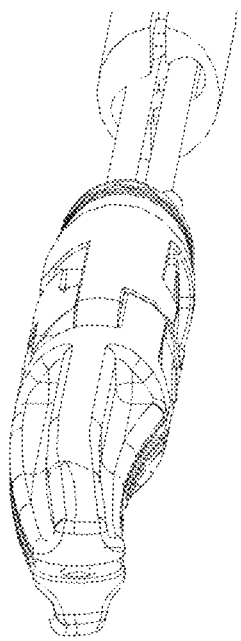
FIG. 19A illustrates exemplary jaws having minimized wall thickness and increased surface area in order to dissipate heat faster which directly reduces the thermal spread on the tissue.
Figure 19B:
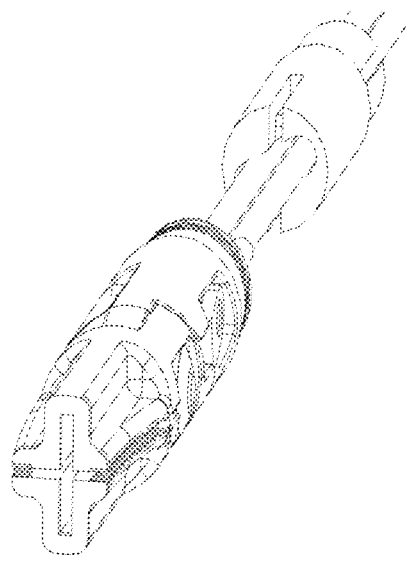
FIG. 19B illustrates a cross sectional view of the jaw assembly as illustrated in FIG. 19A.

FIG. 19A illustrates exemplary jaws having minimized wall thickness and increased surface area in order to dissipate heat faster which directly reduces the thermal spread on the tissue. FIG. 19B illustrates a cross sectional view of the jaw assembly as illustrated in FIG. 19A.

This instrument can be used for various surgical procedures without limitation.

In an embodiment, a vessel sealer having a uniform pressure mechanism, detachable blade/cutter and detachable jaw assembly is disclosed. A bipolar surgical instrument, includes a jaw assembly having jaws connected to an outer tube, wherein the blade is connected to the blade pushing tube through a blade connector; a spring cap operatively engages said blade tube assembly wherein on disengagement of the said jaw assembly from an outer tube and said spring cap from said blade pushing tube are adapted to be detached from each other; a handle assembly, operatively coupled to said jaw assembly comprising a uniform pressure mechanism which contains primary spring, a secondary spring, wherein said uniform pressure mechanism enables closure of the jaws to ensure and exert a uniform pressure on the tissue and/or vessel. small vessels and big vessels can be sealed with uniform pressure, which avoids excessive pressure on bigger vessels and less pressure on small vessels.

In an exemplary embodiment, the handle assembly (5) includes an outer casing (31), an inner casing (32), and a cap (33). In another exemplary embodiment, the inner casing (32) includes a jaw locking balls, a bush, a connector, a secondary spring and a cap. In yet another exemplary embodiment, the outer tube (21) is detached from a first threaded joint (22) provided on said jaw assembly (19) and attached to the jaws (4) and wherein the blade pushing tube (20) is detached from a second threaded joint (23) provided on said jaw assembly (19).

In an exemplary embodiment, the secondary spring (28) is stiffer than the primary spring (29).

In an exemplary embodiment, the jaw locking balls (27), during the operation of said handle assembly (5) for closing the jaws, pushed by the jaw assembly (19) and expands outwardly to a front region of a cam (30).

In an exemplary embodiment, the outer tube (21) is assembled on top of a blade/cutter due such that the blade/cutter is fixed at one position with a blade connector.

In an exemplary embodiment, the blade/cutter is detachable from the blade/cutter connector to enable the blade/cutter to be removed through the jaw assembly.

In an exemplary embodiment, the jaw assembly (19), upon detachment, is cleanable or autoclavable for reuse. The handle assembly (5) by said uniform pressure prevents injury to the tissue and/or vessel and allows only a certain uniform maximum pressure on the tissue and/or vessel to seal it without damaging the other tissue and/or vessel.

I claim:

1. A bipolar surgical instrument, comprising:
    a jaw assembly having jaws connected to an outer tube, wherein a blade is connected to a blade pushing tube through a blade connector;
    a spring cap configured to operatively engage said blade pushing tube, wherein on disengagement of the spring cap, said jaw assembly, said blade pushing tube and said outer tube are adapted to be detached from each other, wherein on the disengagement of the spring cap, the outer tube connected to the jaws is detachable from a first threaded joint provided on said jaw assembly, and wherein the blade pushing tube is detachable from a second threaded joint provided on said jaw assembly; and
    a handle assembly, operatively coupled to said jaw assembly, comprising a uniform pressure mechanism having a primary spring, a secondary spring, wherein said primary spring and said secondary spring enables closure of the jaws to ensure and exert a uniform pressure on a tissue and/or a vessel.

2. The bipolar surgical instrument as claimed in claim 1, wherein said handle assembly includes an outer casing, an inner casing, and a first cap.

3. The bipolar surgical instrument as claimed in claim 2, wherein said inner casing includes jaw locking balls, a bush, a connector, the secondary spring and a second cap.

4. The bipolar surgical instrument as claimed in claim 1, wherein the secondary spring is stiffer than the primary spring.

5. The bipolar surgical instrument as claimed in claim 1, wherein the jaw assembly is configured to move between jaw locking balls and slide the jaw locking balls in locking position to a back of a cam surface to lock the jaw assembly wherein a trigger is configured to be pressed for opening and closing the jaws.

6. The bipolar surgical instrument as claimed in claim 1, wherein the blade is assembled within the outer tube such that the blade is fixed at one position with the blade connector.

7. The bipolar surgical instrument as claimed in claim 6, wherein the blade is detachable from the blade connector to enable the blade to be removed through the jaw assembly.

8. The bipolar surgical instrument as claimed in claim 1, wherein said jaw assembly, upon detachment, is cleanable or autoclavable for reuse.

9. The bipolar surgical instrument as claimed in claim 1, wherein the handle assembly by said uniform pressure prevents injury to the tissue and/or vessel and allows only a certain uniform maximum pressure on the tissue and/or vessel to seal it without damaging another tissue and/or vessel.

* * * * *